(12) United States Patent
Kirts et al.

(10) Patent No.: US 6,640,618 B2
(45) Date of Patent: Nov. 4, 2003

(54) METHOD FOR DETECTING AND MEASURING FOAM FORMING COMPOUNDS IN AQUEOUS SOLUTIONS

(75) Inventors: Richard Eugene Kirts, Oxnard, CA (US); Brad Lee Hollan, Oxnard, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/119,351

(22) Filed: Apr. 10, 2002

(65) Prior Publication Data

US 2002/0116137 A1 Aug. 22, 2002

Related U.S. Application Data

(63) Continuation-in-part of application No. 09/917,565, filed on Jul. 25, 2001, now Pat. No. 6,405,580, which is a continuation-in-part of application No. 09/566,888, filed on May 8, 2000, now Pat. No. 6,397,665.

(51) Int. Cl.[7] .............................. G01N 24/00; G01N 3/32
(52) U.S. Cl. .......................... 73/60.11; 73/579; 73/592; 250/357.1; 436/55
(58) Field of Search .................... 73/60.11, 579, 73/592, 61.41, 64.41, 64.43; 95/155, 157; 210/750; 250/343, 357.1; 436/55

(56) References Cited

U.S. PATENT DOCUMENTS

| 3,151,061 A | * | 9/1964 | Orr | 73/60.11 |
| 5,465,610 A | * | 11/1995 | Loisel | 73/60.11 |
| 5,597,950 A | * | 1/1997 | Mullen | 73/60.11 |

FOREIGN PATENT DOCUMENTS

| DE | 4036344 | * | 5/1992 | 73/60.11 |
| SU | 1302193 | * | 4/1987 | 73/60.11 |

* cited by examiner

Primary Examiner—Daniel S. Larkin
(74) Attorney, Agent, or Firm—David S. Kalmbaugh

(57) ABSTRACT

A method for detecting change in the foam forming characteristic of an input stream of an aqueous solution which continuously samples the input stream by taking a series of discrete, independent measurements. The method relies on an acoustic sensor to measure foam height within a column. A sample of the input stream is introduced into the column, and aerated to produce foam. The height of the column of foam is then measured using the acoustic sensor, which is correlated with the concentration of foam forming chemical.

18 Claims, 9 Drawing Sheets

METHOD FOR DETECTING AND MEASURING FOAM FORMING COMPOUNDS IN AQUEOUS SOLUTIONS

This application is a continuation-in-part of U.S. patent application Ser. No. 09/917,565, filed Jul. 25, 2001, now U.S. Pat. No. 6,405,580, which is a continuation-in-part of patent application Ser. No. 09/566,888, filed May 08, 2000, now U.S. Pat. No. 6,397,665.

BACKGROUND OF THE INVENTION

1. Field of the Invention

The present invention relates generally to a method for detecting the presence of foam forming compounds in aqueous solutions. More particularly, the present invention relates to a method which detects the presence of specific foam forming compounds in an aqueous solution, and, when calibrated, measures the concentration of the foam forming compounds present in the aqueous solution.

2. Description of the Prior Art

Foam forming compounds include cleaning compounds, such as detergents, fire-fighting chemicals, and naturally occurring surfactants, such as plant extractives. The presence of foam forming compounds can interfere with the operation of chemical plants, such as wastewater treatment plants, by causing inaccurate readings in flow and level sensing devices.

Foaming of wastewater tends to lift solid materials out of the liquid phase and suspend the materials in the foam. These solid materials may include metals or other hazardous materials. In open top tanks, pollutant-laden foams may be blown off the surface of the wastewater and onto the surrounding property. Hazards of this type often result in citations from public health offices and environmental protection officials.

Some foam forming chemical are also toxic to the microorganisms used in wastewater treatment plants. Early detection of foam forming chemicals permits process streams contaminated with these chemicals to be diverted from the main process flow. The diverted flow can be subsequently treated in a specialized foam forming agent removal process.

Foam detecting devices used in the past to detect the presence of foam forming chemicals in an aqueous solution cannot rapidly detect a change of state from a foaming input stream to a non-foaming input stream. For example, if a prior art device was measuring the foam forming characteristic of an input stream that contained a high concentration of a foam forming chemical, and then the input stream was changed to a stream that contained little or no foam forming chemical, the prior art device could not rapidly detect the change in input stream composition. This is because the prior art device has a fixed or static solution reservoir at the bottom of the device, and the concentration of the foam forming chemical in that reservoir is changed only by dilution from the input stream. It may take several minutes before a low concentration input stream dilutes the solution in the reservoir to a concentration that no longer forms a significant amount of foam.

Devices used in the past to detect the presence of foam forming chemicals are generally not automated. These devices are manually operated and are best suited to a laboratory environment.

Prior art devices for detecting the presence of foam forming chemicals are also fragile, generally consisting of a piece of custom blown glasswork.

In addition, prior art devices rely on photo-optical sensor pairs to detect and measure the presence of foam at discrete locations. This approach is expensive to implement and provides a limited number of foam height detection values. Also, reliance upon photo-optical pairs to detect the present of foam requires that the column containing the foam be transparent. In some foam sensing applications, a film of oil, algae, bacteria, and other deposits may eventually occlude a clear column. This renders the photo-optical sensors inoperable.

Further, at low concentrations of foam forming chemical, the foam can usually be characterized as being composed of a small number of large bubbles. The beam from a photo-optical sensor can intermittently pass through such loosely structured foam, resulting in intermittent false readings of foam height.

Accordingly, there is a need for an apparatus for detecting and measuring foam forming compounds in aqueous solutions which is accurate, relatively simple in design, and sufficiently strong to avoid breakage and low cost.

SUMMARY OF THE INVENTION

A sample of the liquid or wastewater to be tested enters a vertically positioned tubular column from a fill valve through a column cap at the top of the tubular column, flows down the sides of the column, and collects in a lower portion of the column. The liquid level in the column rises to a liquid level switch. Closing the liquid level switch prevents further flow of liquid into the tubular column.

After a sample of liquid has collected in the lower portion of the column, an air pump is actuated and compressed air flows into the sample through an aeration stone. The air bubbles produced by the aeration stone cause the foam forming compounds in the sample to produce foam. The foam rises in the column and lifts a float which functions as a solid target for an acoustic distance measuring device. The measuring device measures height within the column, generating a continuous analog electrical output signal which is a function of foam height. The value of voltage produced by the measuring device is measured and retained by a programmable logic controller connected to the measuring device.

As the float rises in the sensor tube, a beam of light between photo-optical sensors is encountered and is broken. As the float passes the beam of light, the beam then encounters the foam in the tubular column. If the foam is of sufficient density that it continues to interrupt the beam of light and it continues to lift the ball to a lower set point programmed into the measuring device, a red indicator light is illuminated. If the foam density is insufficient to block the beam of light generated by the optical sensors, the red indicator light does not illuminate and the system recognizes that the aqueous foam forming film concentration is below a predetermined threshold level. When the red indicator light remains illuminated, it indicates that the sample solution contains aqueous foam forming film at or above a predetermined threshold and the apparatus automatically sends a message to alert the user.

After a foam height measurement has been made, the fill valve closes, a sample drain valve opens, and a 3-way valve is positioned to divert compressed air from the aeration stone to the top of the column. This forces the sample of solution and foam from the column through a drain valve. After the solution has been drained from the column, the fill valve opens, the drain valve closes, air is re-directed to the aeration stone, and the entire sample acquisition and measurement cycle is repeated.

DETAILED DESCRIPTION OF THE PREFERRED EMBODIMENT

Figure 1:
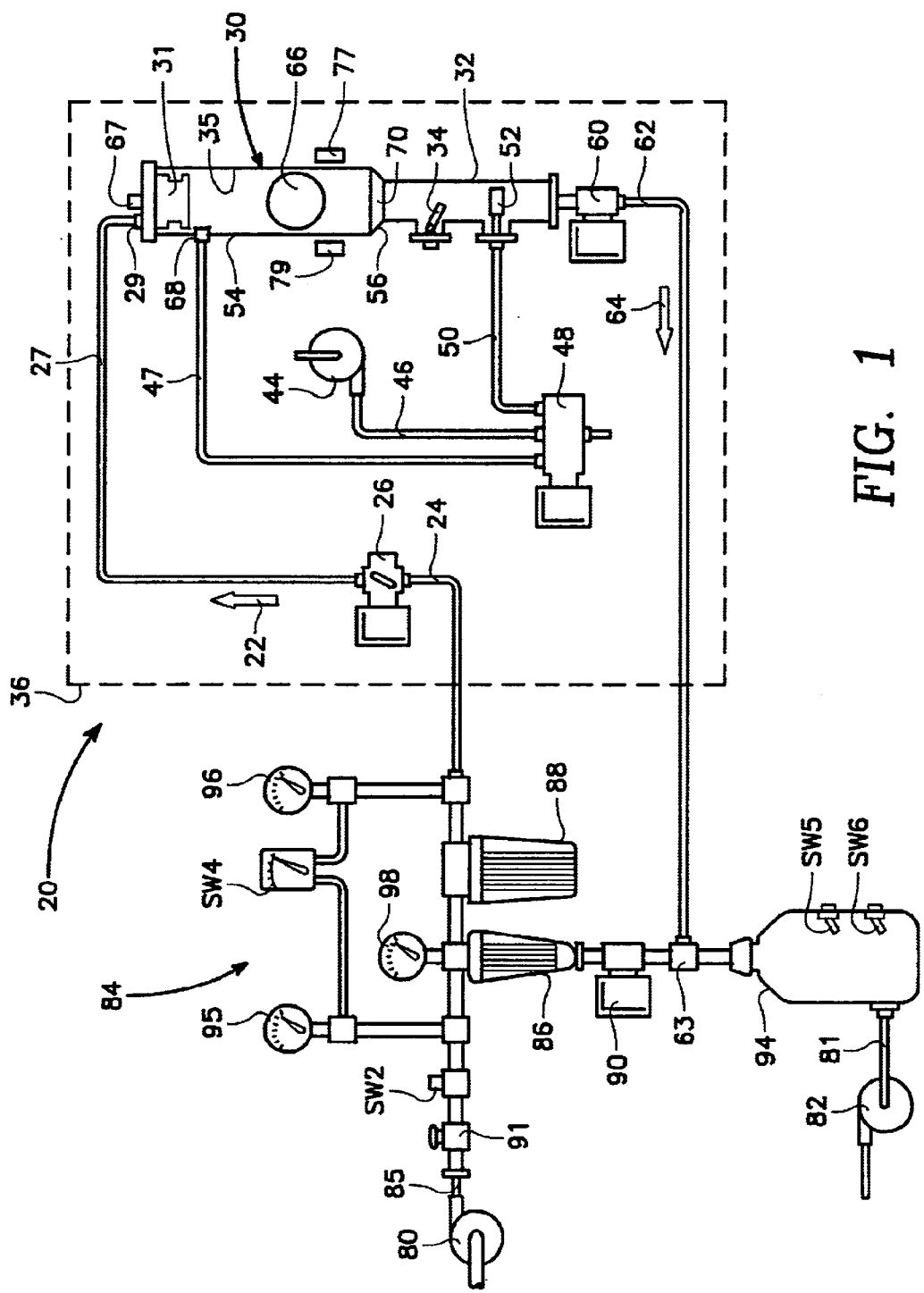
FIG. 1 is a plan view of an apparatus for detecting and measuring foam forming compounds in aqueous solutions comprising the present invention.

Referring first to FIG. 1, there is shown an apparatus, designated generally by the reference numeral 20, which detects the presence of foam forming compounds in aqueous solutions. Apparatus 20, when calibrated also will measure the concentration of specific foam forming compounds in an aqueous solution. Foam forming compounds include cleaning compounds such as detergents, fire fighting chemicals, and naturally occurring surfactants such as plant extractives.

The apparatus 20 comprising the present invention, operates by measuring the foam forming capability of an aqueous solutions with a time series of discrete tests. A sample of an aqueous solution is introduced into apparatus 20. The height of the column of foam is then measured by an apparatus 20 using an acoustic distance-measuring device. The sample of the aqueous solution is then discarded and the sampling process is repeated using apparatus 20. The height of the column of foam is correlated with the concentration of foam forming chemical. The apparatus is capable of detecting fewer than fifteen parts per million of aqueous film forming foam in less than forty-five seconds.

A sample of a liquid or aqueous solutions to be tested enters apparatus 20 through an inlet supply line 24 (as indicated by arrow 22) which includes an electrically operated supply/fill valve 26. When valve 26 is electrically energized, fill valve 26 is opened such that the liquid to pass through water supply line 27 and an opening 29 at the top of a tubular column 30 through a column cap 31 into the tubular column 30. The liquid then flows down the inner wall/sides 35 of tubular column 30, and collects in the bottom or lower portion 32 of tubular column 30.

The liquid level in the lower portion 32 of column 30 rises to the level of a liquid level switch 34. When liquid level switch 34 closes, fill valve 26 is deactivated and the flow of liquid is through fill valve 26 to a drain located on the backside of foam sensor housing 36.

When the sample of the liquid has collected in the lower portion 32 of tubular column 30, an electrically operated air pump 44 is actuated providing compressed air which flows through an air supply line 46 into a three-way electrically operated air valve 48. The compressed air then passes through air valve 48 and an air line 50 into the liquid sample through a porous aeration stone 52 which forms bubbles. The aeration stone 52 is mounted horizontally in the lower portion 32 of tubular column 30 50 that it generates small air bubbles within the sample.

The many small air bubbles generated by aeration stone 52 cause the foam forming compounds in the sample to produce foam. The foam rises in tubular column 30 lifting a spherical-shaped lightweight float/target 66 into the upper portion 54 of tubular column 30. Spherical-shaped lightweight float/target 66 comprises a polystyrene ball.

As depicted in FIG. 1, the upper portion 54 of tubular column 30 is larger in diameter than the lower portion 32 of tubular column 30. Between the upper portion 54 and the lower portion 32 of tubular column 30 is a reducing collar 56. When apparatus 20 is not operational, float 66 rest within the reducing collar 56 of tubular column 30. Reducing collar 56 has a centrally located opening 70 which allows foam to pass through opening 70 to the upper portion of tubular column 30 lifting float 66 in a vertical direction upward within the upper portion 54 of tubular column 30.

Figure 2A:
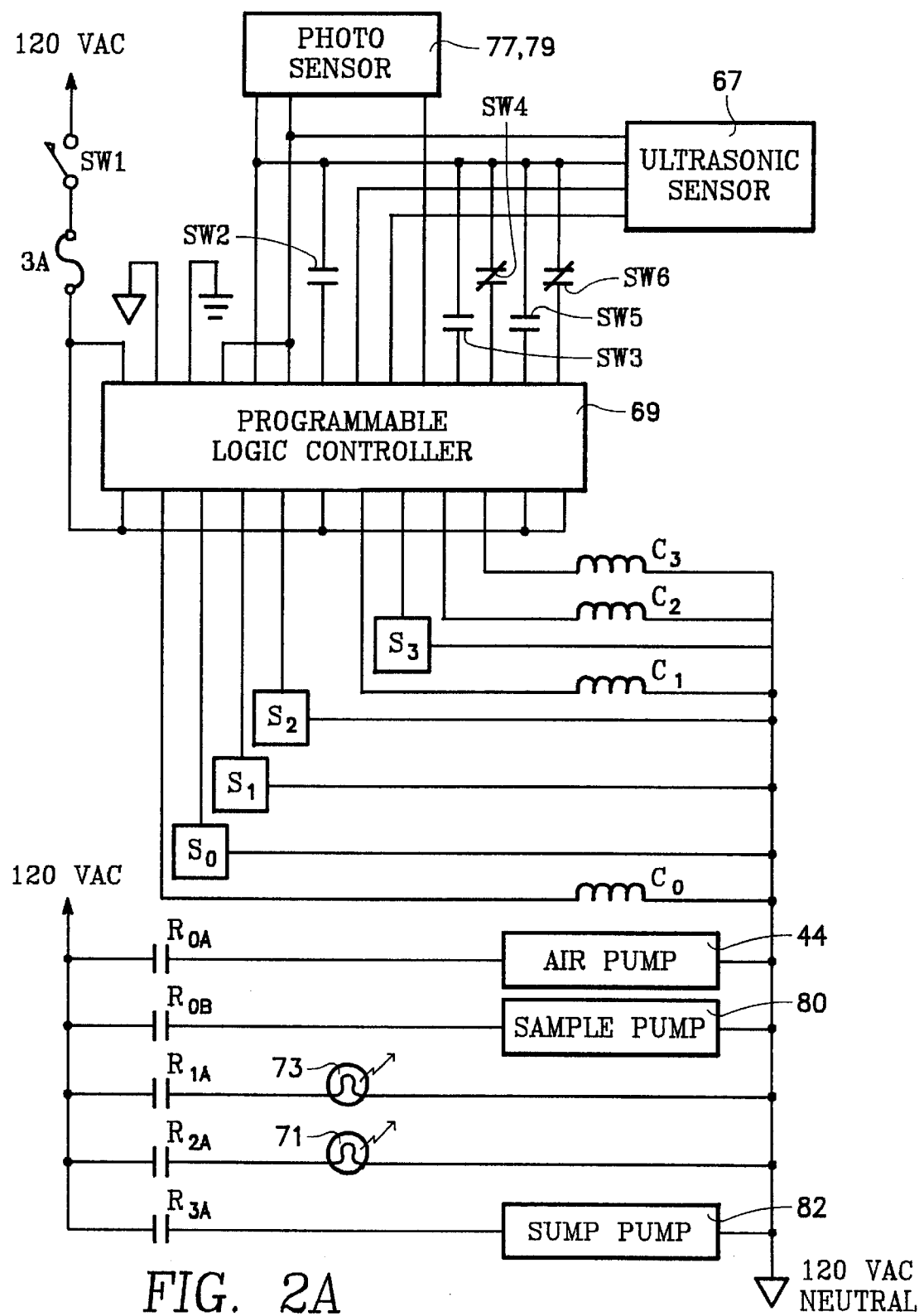
FIGS. 2A–2C is an electrical schematic diagram of the 120 VAC control circuity for the apparatus of FIG. 1.
Figure 2B:
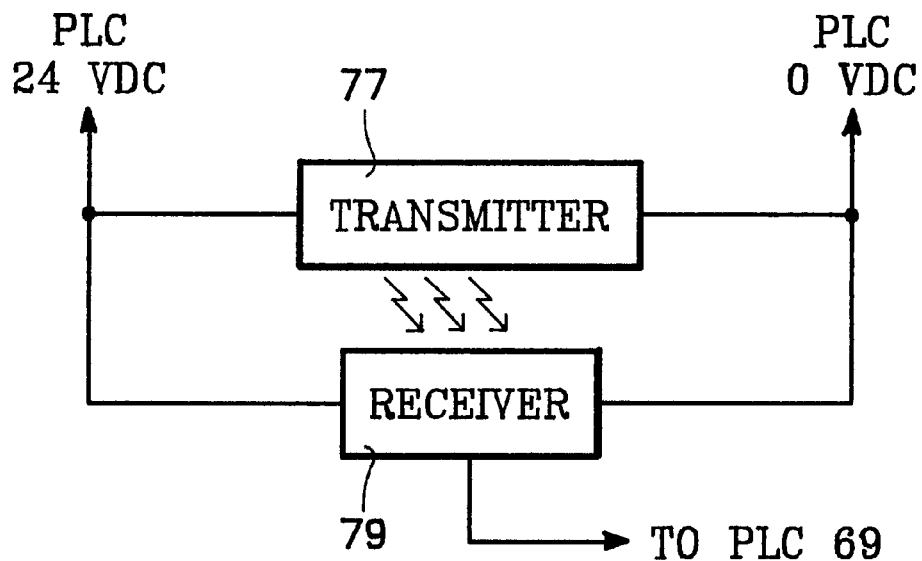

The float 66 serves as a solid target for an acoustic distance measuring device/acoustic sensor 67. The acoustic distance measuring device 67, which is positioned at the top of tubular column 30, measures the height of the column of foam within tubular column 30 by bouncing ultrasonic sound waves off the target 66 and measuring time of travel of the ultrasonic waves to and from the target 66. The acoustic distance measuring device 67 produces a continuous analog electrical output signal which is a function of foam height within tubular column 30. The output signal's voltage value produced by the acoustic distance measuring device 67 is measured, sampled and retained by a sample-and-hold circuit within a programmable logic controller 69 connected to measuring device 67, as shown in FIG. 2A.

The programmable logic controller 69 used in the preferred embodiment is a Model Micro$^3$ Programmable Logic Controller commercially available from IDEC Corporation of San Jose, Calif. Programmable logic controller 69 is programmed using WINDLER software which is commercially available from IDEC Corporation. The WINDLER software includes a monitor mode which allows the user to monitor the logic control program currently running in the programmable logic controller in real time.

At this time it should be noted that a laser distance measuring device could be substituted for the acoustic distance measuring device 67 to perform the function of measuring the height of the foam column within tubular column 30.

It should also be noted that the acoustic distance measuring device used in the present invention is a Model M-5000 Smart Ultrasonic Sensor commercially available from Massa Products Corporation of Hingham, Mass. The Current Loop Output Settings for device are as follows: 0 mA distance is 13 inches, the 20 mA distance is 4.5 inches and the output span is 0–20 mA. The Set point Output Settings are as follows: the close set point distance is 7 inches and the far set point distance is 9 inches. The software for the M-5000 Smart Ultrasonic Sensor allows the user to monitor the performance of the sensor in real time. A status panel which appears on an external computer screen indicates the real time distance from the ultrasonic sensor to the target.

If float 66 rises above a predetermined set point within the portion 54 of tubular column 30, an alarm is activated. The alarm that is activated comprises a red indicator light 71, shown in FIG. 2A.

After a foam height measurement within tubular column 30 has been made, an electrically operated sample drain valve 60 opens (i.e. is deactivated) and the sample drains from column 30 through valve 60 and a drain pipe 62 (as indicated by arrow 64).

Simultaneously, with the opening of valve 60, valve 48 is deactivated which diverts compressed air provided by air pump 44 through an air supply line 47 to an opening positioned within the upper portion 54 of tubular column 30. The opening 68 is positioned immediately below column cap 31 within tubular column 30. Compressed air supplied through opening 68 forces the sample and foam out of tubular column 30 through drain valve 62 and drain pipe 64.

After the foam forming solution has been drained from tubular column 30, valve 60 is activated or closed, valve 26 is again activated and the sample acquisition cycle is repeated.

There is also mounted within foam sensor housing 36 a pair of photo-optical sensors 77 and 79 which are in alignment on opposite sides of the upper portion 54 of tubular column 30. The pair of photo-optical sensors 77 and 79 allow an operator of apparatus 20 to obtain supplementary measurements of foam density within tubular column 30. When the foam within tubular column 30 has a low density, that is the foam consists of a few large bubbles, the beam of light from the transmitter of the pair of photo-optical sensors 77 and 79 will pass through the foam to the receiver of the pair of photo-optical sensors 77 and 79.

When, however, the foam within tubular column 30 has a high density, that is the foam consists of many small bubbles, the beam of light from the transmitter of the pair of photo-optical sensors 77 and 79 will not pass through the foam to the receiver of the pair of photo-optical sensors 77 and 79. The data provided by the pair of photo-optical sensors 77 and 79 relative to foam density is then combined with data from acoustic distance measuring device 67 to provide an accurate and reliable measurement of foam quality. The data provided by optical sensor 79 to programmable logic controller 69 is in the form of a direct current voltage signal.

Referring to FIGS. 1 and 2A–2C, programmable logic controller 69 controls the operation of apparatus 20. A power on switch SW1 when set to the ON position supplies 120 VAC through fuse 3A to programmable logic controller 69. Programmable logic controller 69, in turn, supplies 24 VDC to transmitter 77 and receiver 79 illustrated in FIG. 2B. Acoustic distance measuring device 67 and photo-optical receiver 79 are connected to programmable logic controller 69 to provide electrical signals to controller 69 indicative of foam quality in the upper portion 54 of tubular column 30.

Programmable logic controller 69 provides electrical signals to coils $C_0$, $C_1$, $C_2$ and $C_3$ to activate coils. When, for example, coil $C_0$ is energized, contacts $R_{OA}$ and $R_{OB}$ are closed. This activates air pump 44 and a sample pump 80 which is used to supply samples of the liquid to apparatus 20 for testing for the presence of foam in the samples.

When programmable logic controller 69 energizes coil $C_1$, contact $R_{1A}$ closes activating light 73. Similarly, when programmable logic controller 69 energizes coil $C_2$, contact $R_{2A}$ closes activating light 71. Energizing coil $C_3$ closes contact $R_{3A}$ which activates an external sump pump 82. Programmable logic controller 69 also provides activation signals to solenoid $S_0$, solenoid $S_1$, and solenoid $S_2$. Solenoid $S_0$ is the solenoid for supply valve 26, solenoid $S_1$ is the solenoid for air valve 48, and solenoid $S_2$ is the solenoid for drain valve 60.

Referring to FIG. 1, there is shown an oil water separator 84 which supplies water samples to apparatus 20 via inlet supply line 24 and electrically operated supply valve 26. The oil water separator 84 comprises an inlet line 85 which includes a shut off valve 91 and a flow direction sensing switch SW2; a backwash strainer 86 for removing large particulate matter; and a filter 88 equipped with an oleophilic element. The oil water separator 84 also has a pair of pressure gauges 95 and 96 and a pressure gauge 98 operatively coupled to the backwash strainer 86.

Figure 2C:
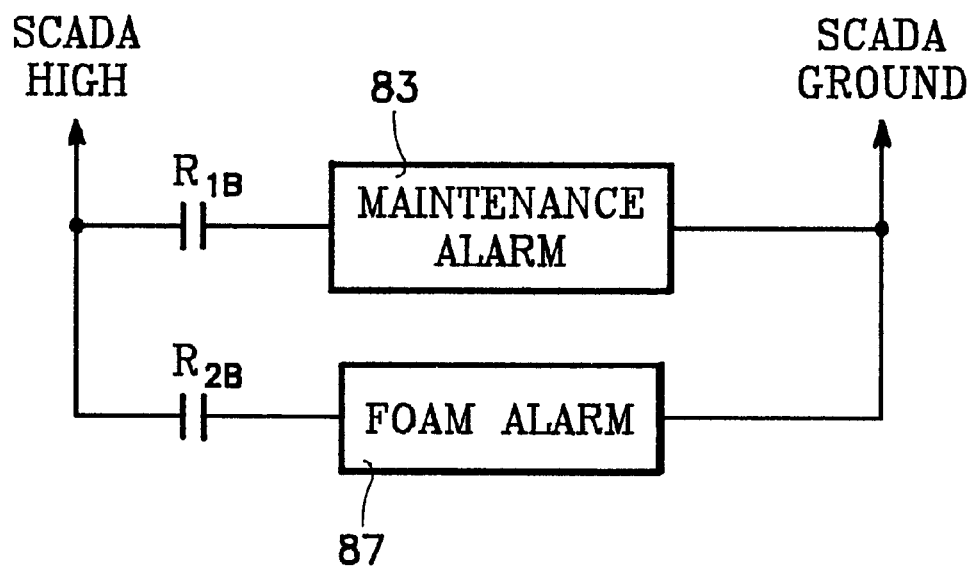
Figure 3A:
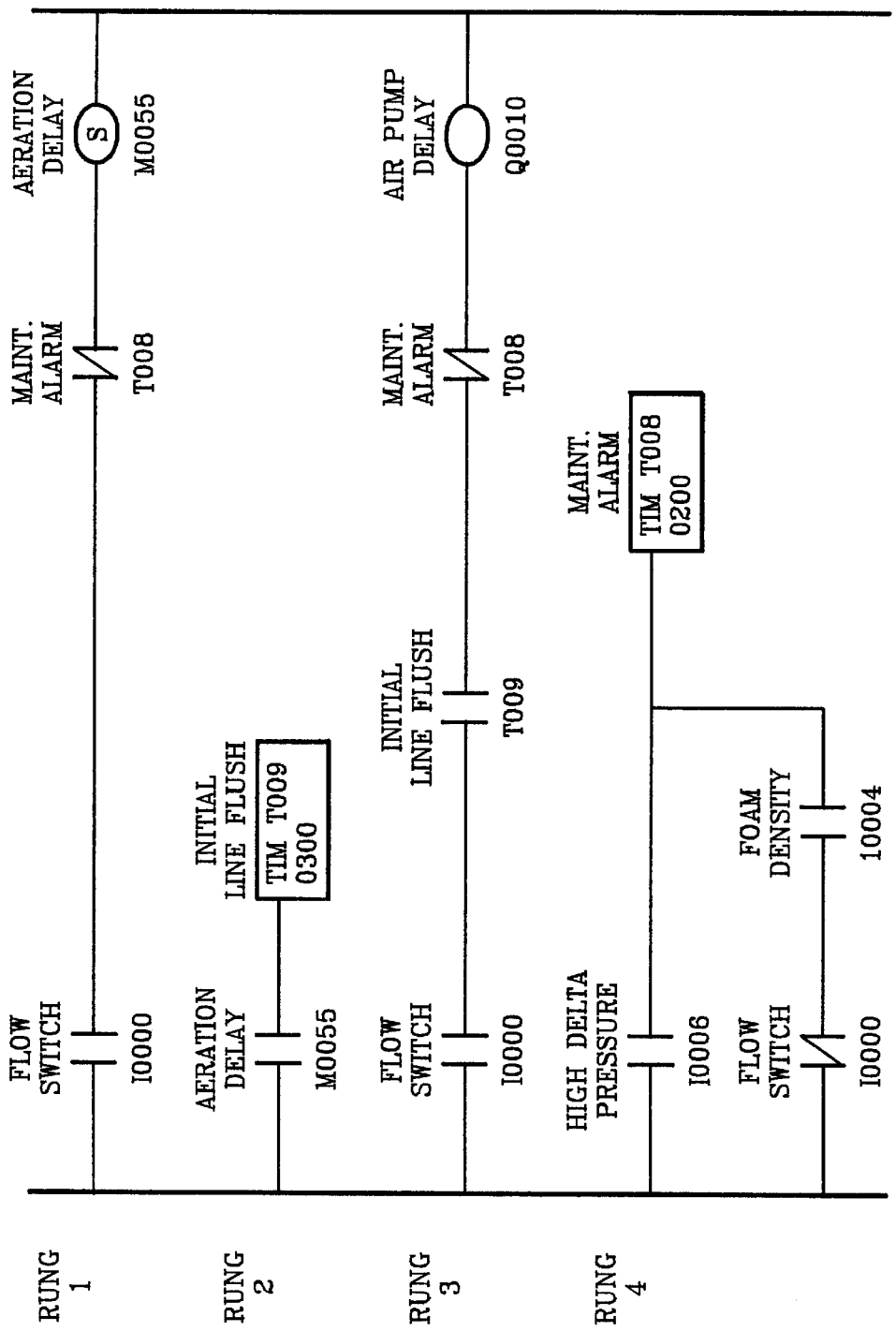
FIGS. 3A–3F is an electrical schematic diagram which illustrates the relay logic circuitry for the programmable logic controller of the apparatus of FIG. 1.
Figure 3B:
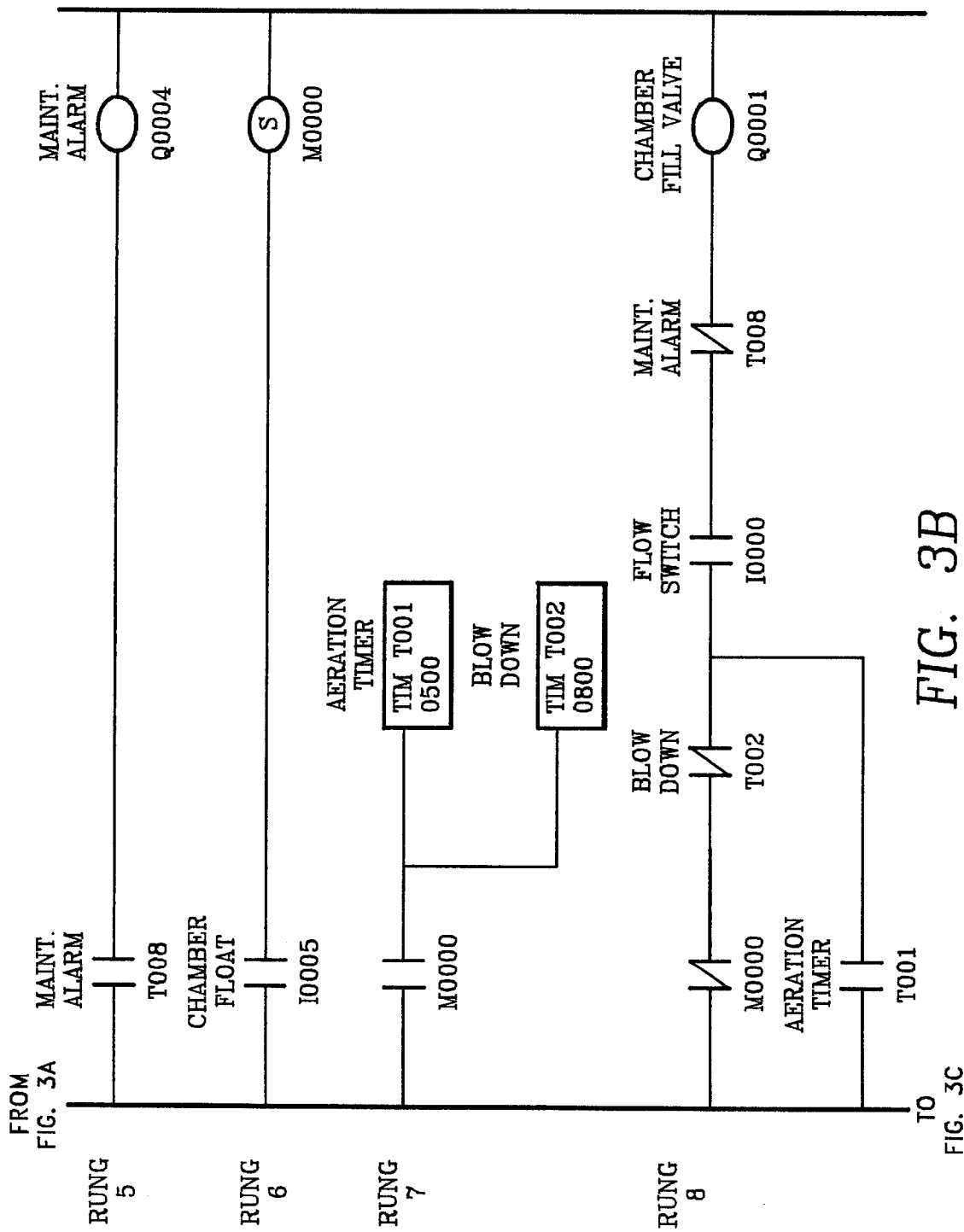
Figure 3C:
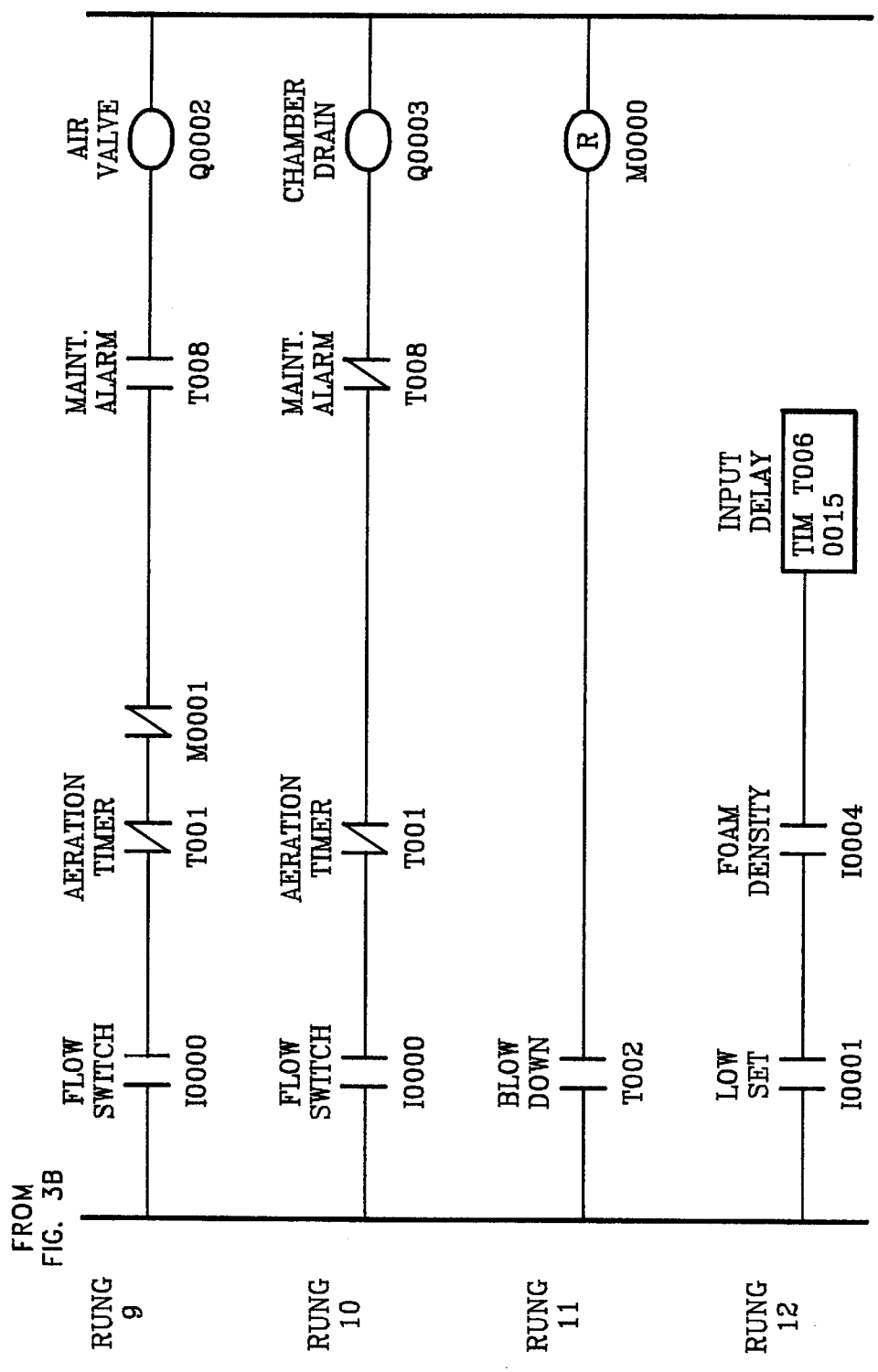
Figure 3D:
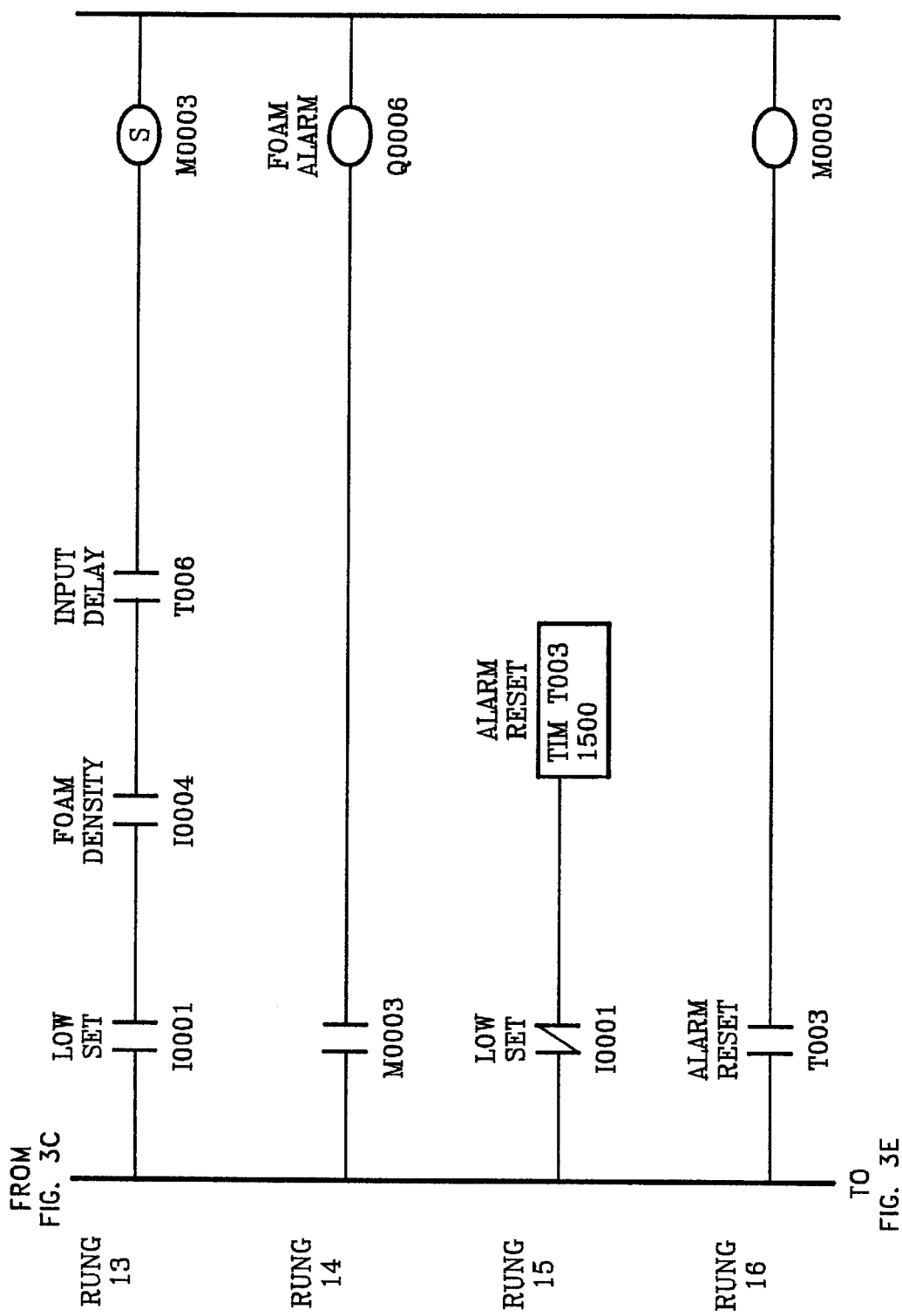
Figure 3E:
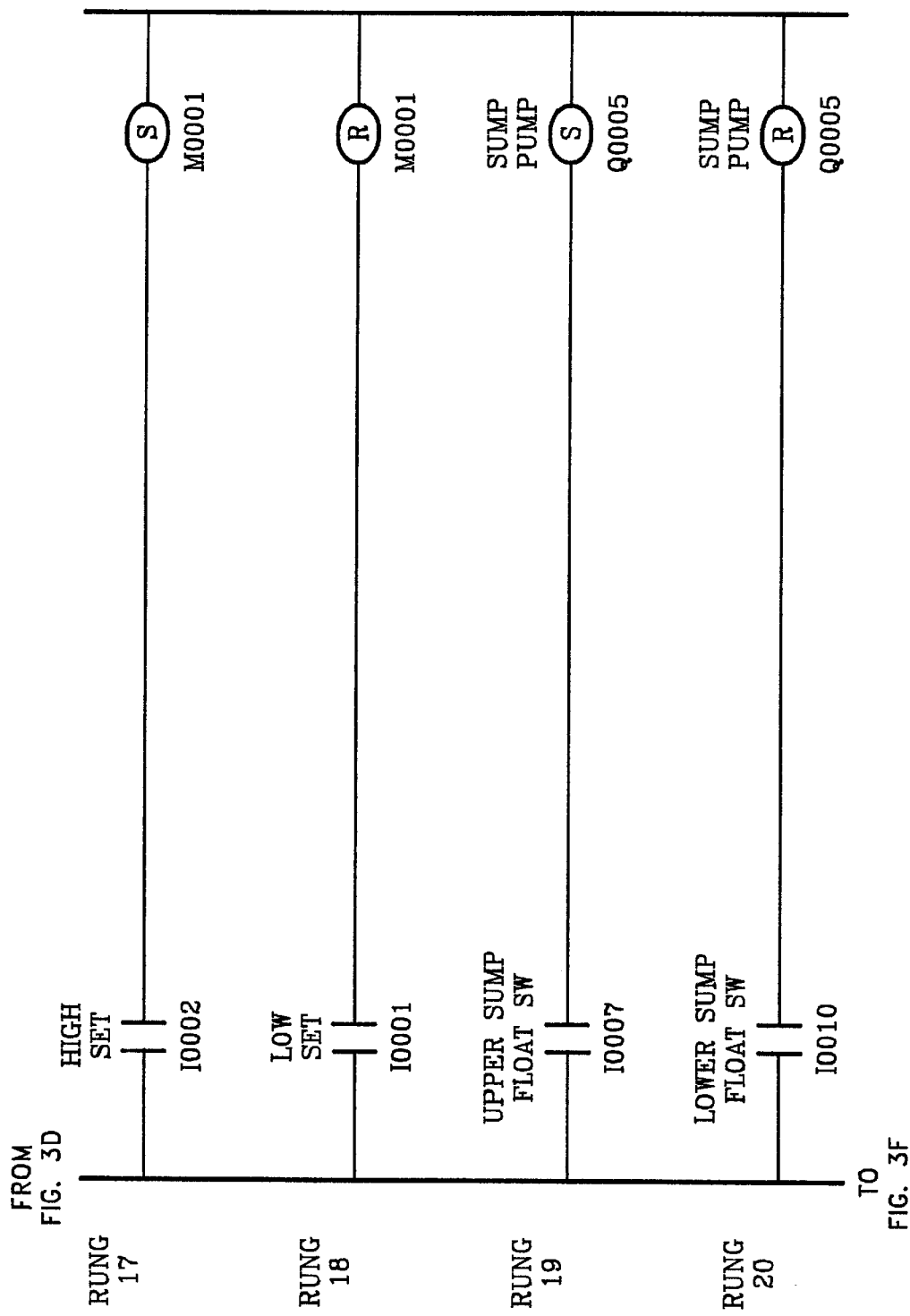
Figure 3F:
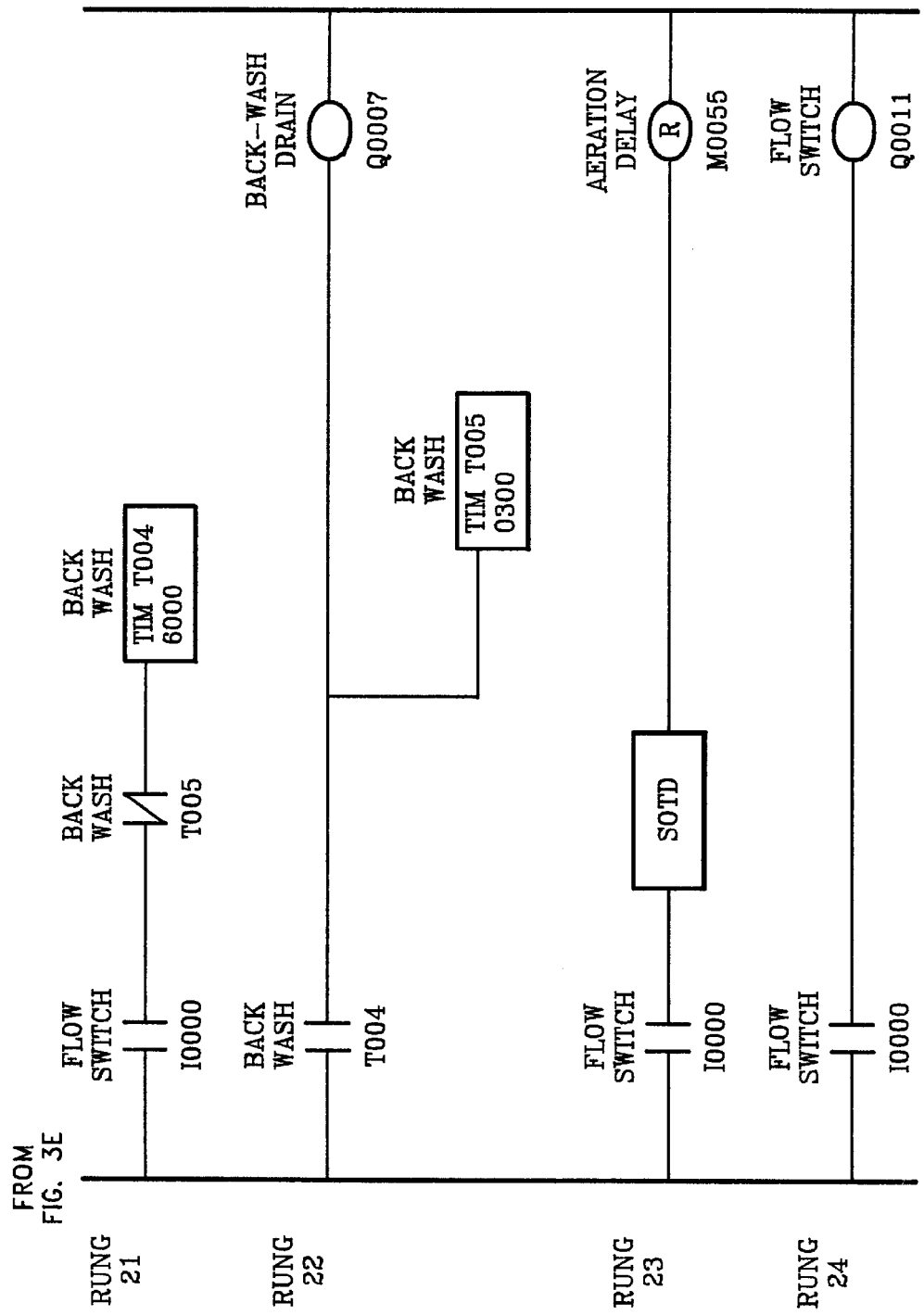

The filter 88 removes oil from the water samples. Oil water separator 84 also includes a backwash valve 90 which has a solenoid 53 connected to programmable logic controller 69. Periodically reversing the water flow through backwash strainer 86 is required to clean strainer 86. The backwash interval and duration is controlled by programmable logic controller 69 which energizes the solenoid S3 of backwash valve 90 to clean backwash strainer 86. Activation of maintenance alarm 83 require closure of contact $R_{1B}$ which is illustrated in FIG. 2C.

The oleophilic element of filter 88 will eventually plug up and have to be replaced. A plugged filter results in an increase in pressure drop across filter 88. When this occurs, a differential pressure switch SW4 sends an electrical signal to programmable logic controller 69 indicating that the oleophilic element of filter 88 needs replacement. Apparatus 20 is designed to automatically shut down and alert the user of apparatus that the oleophilic element of filter 88 needs replacement. The illumination of amber lamp 73 indicates that maintenance is required.

Referring to FIGS. 1 and 2A, electrical signals for a sump pump 82 and backwash valve 90 are provided by programmable logic controller 69. The sump pump 82 is connected to a holding tank 94 via a fluid flow line 81. Holding tank 94 has mounted thereon an upper float switch SW5 and a lower float switch SW6. The holding tank 94 is connected via a T-shaped pipe connector 63 to drain pipe 62 to receive the samples of the aqueous solution, i.e. wastewater being tested. Backwash valve 90 is also connected to holding tank 94 via connector 63.

When the holding tank 94 is full switch SW5 closes sending a signal to programmable logic controller 69 which turns on sump pump 82. When the liquid level in holding tank 94 reaches a low water level switch SW6 closes sending a signal to programmable logic controller 69 which turns off sump pump 82.

While apparatus 20 is operational, many different events can occur. The sequence of events during normal operation of the apparatus 20 are illustrated by the following example. Bilge water is pumped from a ship to an oily-waste lift station. Assume for this example that the wastewater contains 50 ppm Aqueous Foam Forming Film (AFFF). As the sump in the lift station fills, large wastewater transfer pumps are energized to move the wastewater from a collection point to a wastewater treatment plant.

A small portion or sample of the waste stream is diverted to the apparatus 20. Flow direction sensing switch SW2 installed in the oil water separator 84 signals apparatus 20 to begin the wastewater sampling process. Fluid direction sensing switch SW2 is adapted to detect the flow of liquid through separator 84. Fluid direction sensing switch SW2 is connected to programmable logic controller 69.

The programmable logic controller 69 continuously loops through its set of instructions. Therefore, controller 69 is not necessarily at the beginning of the program cycle when the apparatus 20 receives the signal from the flow direction sensing switch SW2. However, for this example we will assume the apparatus 20 starts at the beginning of a fill cycle.

With the fill valve 26 energized, flow is directed to the top of the tubular column 30. The sample flows into the cap 31 on the top of the tubular column 30 and runs down the wall of the tubular column 30. Water fills the chamber formed within the bottom portion 32 of the tubular column 30 until the liquid level switch 34 in the chamber closes. When the chamber is full, fill valve 26 is de-energized and the wastewater flow is bypassed to the sump/holding tank 94 through valve 90 which is connected to sump 94.

After an initial delay (to flush the pipes of the previous sample of wastewater), the air pump 44 is activated and air flows through the air valve 48 to the aeration stone 52. Aeration occurs for a predetermined length of time and foam is generated in the tubular column 30. As the foam rises in the tubular column 30, the foam lifts a polystyrene ball 66. The ball 66 provides a firm target for acoustic distance measuring device 67, which measures the distance to the target ball 66. Because the wastewater sample contains 50 ppm AFFF, sufficient foam will be generated in the column for the target 66 to reach a sensor set point.

As the target 66 rises in the sensor tube, the beam of light between photo-optical sensors 77 and 79 is broken. As the target 66 passes the beam, the beam then encounters the foam in the tubular column 30. If the foam is of sufficient density that it continues to interrupt the beam of light and it continues to lift the ball to a lower set point programmed into the acoustic sensor 67, red indicator light 71 is illuminated. If the foam density is insufficient to block the beam from the optical sensors 77 and 79, the red indicator light 71 does not illuminate, and the system recognizes that the AFFF concentration is below a predetermined threshold level. When the red indicator light 71 is illuminated, it indicates that the sample solution contains AFFF at or above a predetermined threshold and apparatus 20 automatically sends a message to alert the user which may be, for example a plant operator. As soon as the red indicator light 71 is illuminated, an internal timer in the control program for programmable logic controller 69 begins a count down. The target 66 must reach the lower set point during the next sample cycle before the timer expires or the red indicator light 71 will go out. If the ball continues to rise to a second high alarm programmed into the acoustic sensor 67, air is diverted from the aeration stone 52 to the top of the tubular column through opening 68. This prevents the target and foam from rising further and contacting the acoustic sensor 67.

After a predetermined length of time, the apparatus 20 enters a wash-down cycle. The drain valve 60 is opened, sample flow is redirected to the top of the tubular column 30, and air is redirected from the aeration stone 52 to the top of the column 30 through opening 68. The sample is flushed out the drain valve 60 in the bottom of the tubular column 30 and flows into the sump 94. Air pressure in the top of the column 30 helps expel the sample from apparatus 20. When the wash-down cycle is finished, the drain valve 60 closes and a new wastewater sample fills tubular column 30.

This process is repeated until the sample no longer contains a high enough concentration of AFFF in the wastewater to cause the target 66 to reach the low set point before the internal timer within programmable logic controller 69 expires. When this occurs, the red indicator light 71 no longer illuminates and a message is sent via an SCADA system interface that the foam event has ended.

The SCADA system (Supervisory Control and Data Acquisition) reports the presence of AFFF foam in the wastewater to a central monitoring facility, such as the wastewater treatment plant.

The foam concentration measuring process performed by apparatus 20 will also stop when the flow direction sensing switch SW2 signals the apparatus 20 that fluid flow is no longer present in the wastewater transfer discharge line. When this occurs, the apparatus 20 is automatically switched off.

Referring to FIGS. 3A–3F, there is shown a ladder logic diagram for programmable logic controller 69. The programmable logic controller 69 activates and de-activates the mechanical and electrical elements of apparatus 20. For example to activate the air pump 44, the flow switch SW2 must be closed and an initial line flush must occur closing flow switch contact 10000 and initial line flush contact T009. This results in activation of Air Pump Relay Q0010 which turns on air pump 44. The ladder logic on Rungs 1, 2 and 3 must be activated to activate air pump 44.

Rungs 4 and 5 turn on a maintenance alarm 83 if (1) there is a high filter delta pressure for filter 88 (2) the optical path is obscured for optical sensors 77 and 79.

Rungs 6 and 7 start aeration and blow down timers on the closure of switch 34. Rung 8 closes fill valve 26 if apparatus 20 is in an aeration cycle and opens the valve 26 for a blow down or maintenance alarm. Rung 9 closes valve 48 during an aeration cycle and a bypass occurs during an initial line flush and a maintenance alarm. Rung 10 closes valve 60 during aeration. Rung 11 activates a blow down. Rung 12 delays the inputs from sensors 77 and 79 for a predetermined time period to minimize false signals.

Rungs 13 and 14 set foam alarm 87 when the float 66 is above a low set point and foam density is high. Activation of foam alarm 87 requires closure of contact $R_{2B}$ which is illustrated in FIG. 2C. Rung 15 and 16 reset foam alarm 87 when float 66 falls below a low set point, a reset timer is started and float 66 fails to rise to the low set point before the reset timer expires.

Rung 17 sets an internal relay if a high set point has been reached. Compressed air is diverted to the top of column Rung 19 turns on sump pump 82 when upper float switch SW5 closes, while rung 20 turns off sump pump 82 when lower float switch SW6 closes.

Rungs 21–24 are used to control a backwash process. Programmable logic controller 69 periodically actuates the solenoid $S_3$ of backwash valve 90. Actuating the solenoid $S_3$ of backwash valve 90 results in wastewater inflow being diverted through valve 90 washing off accumulated dirt and other solid particles from backwash strainer 86. The accumulated dirt and other solid particles then pass through backwash valve 90 into holding tank 94 where the wastewater can be pumped to a drain using pump 82.

The apparatus 20 is capable of detecting the presence of concentrations of aqueous film forming foam in bilge water as low as fifteen parts per million in approximately forty-five seconds.

From the foregoing, it may readily be seen that the present invention comprises a new, unique, and exceedingly useful system for detecting and measuring the concentration of foam forming compounds in aqueous solutions which constitutes a considerable improvement over the known prior art. Many modifications and variations of the present invention are possible in light of the above teachings. It is to be understood that within the scope of the appended claims the invention may be practiced otherwise than as specifically described.

What is claimed is:

1. A method for detecting and measuring foam in wastewater, comprising the steps of:
   generating a plurality of control signals;
   introducing a sample of said wastewater through a fill valve into a vertically positioned tubular column having an inner wall, a first of said plurality of control signals opening said fill valve to allow said wastewater to pass through said fill valve into said tubular column and flow down the inner wall of said tubular column to a lower portion of said tubular column;
   generating a compressed gas, said compressed gas being generated by an electrically operated pump activated by a second of said plurality of control signals;

providing said compressed gas through an air valve to an aeration stone positioned in the lower portion of said tubular column;

generating air bubbles within said wastewater causing a formation of said foam within said tubular column, said air bubbles being generated by air flow through said aeration stone when said compressed gas, responsive to a third of said plurality of control signals passes through said air valve to said aeration stone;

raising a spherical-shaped float positioned within said tubular column in an upward direction within said tubular column, said spherical-shaped float being raised within said tubular column by the formation of said foam within said tubular column;

generating ultrasonic waves, said ultrasonic waves being generated by an ultrasonic sensor positioned at the top of said tubular column;

measuring a time of travel for said ultrasonic waves between said ultrasonic sensor and said spherical-shaped float by bouncing said ultrasonic waves off of said spherical-shaped float;

generating an analog signal which is a function of foam height within an upper portion of said tubular column, said ultrasonic sensor generating said analog signal in response to continuous measurement of the time of travel of said ultrasonic waves between said ultrasonic sensor and said spherical-shaped float;

directing a beam of light through the upper portion of said tubular column, said beam of light when directed through the upper portion of said tubular column providing an indication of a density for said foam within the upper portion of said tubular column; and generating a foam density indicating signal representative of the density of said foam within the upper portion of said tubular column.

2. The method of claim 1 further comprising the steps of:

opening a drain valve located at the bottom of said tubular column; and deactivating said air valve which diverts said compressed gas from said aeration stone through a fluid passageway to an opening within the upper portion of said tubular column forcing said wastewater and said foam out of said tubular column through said drain valve when said drain valve is open.

3. The method of claim 2 wherein a fourth of said plurality of control signals opens said drain valve allowing said wastewater and said foam to drain from said tubular column through said drain valve.

4. The method of claim 1 wherein said plurality of control signals are generated by a programmable logic controller.

5. The method of claim 1 wherein said compressed gas comprises compressed air.

6. The method of claim 1 further comprising the step of processing said analog signal and said foam density indicating signal to generate an alarm signal.

7. The method of claim 6 wherein said alarm signal activates a red indicator light whenever said spherical-shaped float rises above a predetermined set point within the upper portion of said tubular column.

8. The method of claim 1 further comprising the step of removing oil from the sample of said wastewater.

9. The method of claim 8 wherein a filter having an oleophilic element removes the oil from the sample of said wastewater.

10. A method for detecting and measuring foam in wastewater, comprising the steps of:

generating a plurality of control signals, said plurality of control signals being generated by a programmable logic controller;

introducing a sample of said wastewater through a fill valve into a vertically positioned tubular column having an inner wall, a first of said plurality of control signals opening said fill valve to allow said wastewater to pass through said fill valve into said tubular column and flow down the inner wall of said tubular column to a lower portion of said tubular column;

generating a compressed gas, said compressed gas being generated by an electrically operated pump activated by a second of said plurality of control signals;

providing said compressed gas through an air valve to an aeration stone positioned in the lower portion of said tubular column;

generating air bubbles within said wastewater causing a formation of said foam within said tubular column, said air bubbles being generated by air flow through said aeration stone when said compressed gas, responsive to a third of said plurality of control signals passes through said air valve to said aeration stone;

raising a spherical-shaped float positioned within said tubular column in an upward direction within said tubular column, said spherical-shaped float being raised within said tubular column by the formation of said foam within said tubular column;

generating ultrasonic waves, said ultrasonic waves being generated by an ultrasonic sensor positioned at the top of said tubular column;

measuring a time of travel for said ultrasonic waves between said ultrasonic sensor and said spherical-shaped float by bouncing said ultrasonic waves off of said spherical-shaped float;

generating an analog signal which is a function of foam height within an upper portion of said tubular column, said ultrasonic sensor generating said analog signal in response to continuous measurement of the time of travel of said ultrasonic waves between said ultrasonic sensor and said spherical-shaped float;

directing a beam of light through the upper portion of said tubular column, said beam of light when directed through the upper portion of said tubular column providing an indication of a density for said foam within the upper portion of said tubular column;

generating a foam density indicating signal representative of the density of said foam within the upper portion of said tubular column;

opening a drain valve located at the bottom of said tubular column; and deactivating said air valve which diverts said compressed gas from said aeration stone through a fluid passageway to an opening within the upper portion of said tubular column forcing said wastewater and said foam out of said tubular column through said drain valve when said drain valve is open, a fourth of said plurality of control signals opening said drain valve allowing said wastewater and said foam to drain from said tubular column through said drain valve.

11. The method of claim 10 wherein a pair of photo-optical sensors positioned in alignment on opposite sides of the upper portion of said tubular column measures the density of said foam within the upper portion of said tubular column, said pair of photo-optical sensors generating said foam density indicating signal representative of the density of said foam within the upper portion of said tubular column.

12. The method of claim 11 wherein said compressed gas comprises compressed air.

13. The method of claim 10 further comprising the step of processing said analog signal and said foam density indicating signal to generate an alarm signal, said alarm signal activating a red indicator light whenever said spherical-shaped float rises above a predetermined set point within the upper portion of said tubular column.

14. The method of claim 11 further comprising the step of removing oil from the sample of said wastewater, wherein a filter having an oleophilic element removes the oil from the sample of said wastewater.

15. A method for detecting and measuring foam in wastewater, comprising the steps of:

generating a plurality of control signals, said plurality of control signals being generated by a programmable logic controller;

introducing a sample of said wastewater through a fill valve into a vertically positioned tubular column having an inner wall, a first of said plurality of control signals opening said fill valve to allow said wastewater to pass through said fill valve into said tubular column and flow down the inner wall of said tubular column to a lower portion of said tubular column;

generating a compressed gas, said compressed gas being generated by an electrically operated pump activated by a second of said plurality of control signals;

providing said compressed gas through an air valve to an aeration stone positioned in the lower portion of said tubular column;

generating air bubbles within said wastewater causing a formation of said foam within said tubular column, said air bubbles being generated by air flow through said aeration stone when said compressed gas, responsive to a third of said plurality of control signals passes through said air valve to said aeration stone;

raising a spherical-shaped float positioned within said tubular column in an upward direction within said tubular column, said spherical-shaped float being raised within said tubular column by the formation of said foam within said tubular column;

generating ultrasonic waves, said ultrasonic waves being generated by an ultrasonic sensor positioned at the top of said tubular column;

measuring a time of travel for said ultrasonic waves between said ultrasonic sensor and said spherical-shaped float by bouncing said ultrasonic waves off of said spherical-shaped float;

generating an analog signal which is a function of foam height within an upper portion of said tubular column, said ultrasonic sensor generating said analog signal in response to continuous measurement of the time of travel of said ultrasonic waves between said ultrasonic sensor and said spherical-shaped float;

directing a beam of light through the upper portion of said tubular column, said beam of light when directed through the upper portion of said tubular column providing an indication of a density for said foam within the upper portion of said tubular column, wherein a pair of photo-optical sensors positioned in alignment on opposite sides of the upper portion of said tubular column measures the density of said foam within the upper portion of said tubular column, said pair of photo-optical sensors generating said foam density indicating signal representative of the density of said foam within the upper portion of said tubular column;

generating a foam density indicating signal representative of the density of said foam within the upper portion of said tubular column, wherein one of said pair of photo-optical sensors generates said foam density indicating signal representative of the density of said foam within the upper portion of said tubular column;

opening a drain valve located at the bottom of said tubular column; and deactivating said air valve which diverts said compressed gas from said aeration stone through a fluid passageway to an opening within the upper portion of said tubular column forcing said wastewater and said foam out of said tubular column through said drain valve when said drain valve is open, a fourth of said plurality of control signals opening said drain valve allowing said wastewater and said foam to drain from said tubular column through said drain valve.

16. The method of claim 15 wherein said compressed gas comprises compressed air.

17. The method of claim 15 further comprising the step of processing said analog signal and said foam density indicating signal to generate an alarm signal, said alarm signal activating a red indicator light whenever said spherical-shaped float rises above a predetermined set point within the upper portion of said tubular column.

18. The method of claim 15 further comprising the step of removing oil from the sample of said wastewater, wherein a filter having an oleophilic element removes the oil from the sample of said wastewater.

* * * * *